United States Patent [19]

Reiss

[11] Patent Number: 4,938,926

[45] Date of Patent: Jul. 3, 1990

[54] TEST DEVICE FOR CHLORINE MEASUREMENT AND METHOD OF MAKING AND USING SAME

[76] Inventor: Andre Reiss, 147-47 Village Rd., Jamaica, N.Y. 11435

[21] Appl. No.: 300,297

[22] Filed: Jan. 23, 1989

[51] Int. Cl.$^5$ .................. G01N 21/00; G01N 21/75; G01N 33/00
[52] U.S. Cl. ........................................ 422/58; 422/61; 436/124; 436/125; 436/164; 436/165; 436/166
[58] Field of Search ................... 422/58, 61; 436/125, 436/164, 165, 166, 124

[56] References Cited

U.S. PATENT DOCUMENTS 4,795,611 1/1989 van der Smissen ................ 436/124

FOREIGN PATENT DOCUMENTS 1001507 1/1957 Fed. Rep. of Germany .

Primary Examiner—Barry S. Richman
Assistant Examiner—Thalia P. Vassilatos

[57] ABSTRACT

A test device for colorimetric measurement of chlorine in disinfectant water comprising an iodometric reagent enclosed within a reducing fluid incorporated within a valved enclosure.

7 Claims, No Drawings

TEST DEVICE FOR CHLORINE MEASUREMENT AND METHOD OF MAKING AND USING SAME

FIELD OF THE INVENTION

This invention relates to a test device and process for the colorimetric measurement of chlorine and method for the making and use of said device.

BACKGROUND OF THE INVENTION

Chlorine is universally used as a disinfectant for water at the critical level of 1-2 ppm. Field colorimetric methods for the measurement of this level chlorine are based on the chlorination of the organic chromophores DPD and orthotolidine. DPD is expensive, orthtolidine highly toxic; both are used by necessity rather than by choice.

A laboratory method for measuring chlorine level is the well known iodometric proceedure: potassium iodide reacted with chlorinated sample water to produce iodine, the iodine then measured by titration against a primary standard using disappearance of starch-iodine chromophore as the end point. Just combining starch and iodide solution as a colorimetric reagent without use of a back titrant has not worked. Combined aqueous starch/iodide solution is not stable, not sensitive enough to critical chlorine level, and over sensitive to interferents as a test reagent.

A stable, sensitive, interferent shielded iodometric test device for the measurement of chlorine in disinfectant water is the subject of my invention. An object of my invention is a method for making a safe and cheap test composition for colorimetric measurement of chlorine comprising starch/iodide reagent incorporated within a reducing fluid, the reducing fluid stabilizing said starch/iodide reagent, the fluid serving as a propellant to discharge such reagent in atomised form thereby improving such reagent in sensitivity, and the fluid serving as a shield against interferents by propelled entrainment within such discharge reagent. Another object of my invention is a method for packaging such composition within a valved enclosure, thereby making a suitable test device for chlorine measurement. Yet another object of my invention is a method for using said test device to colorimetrically measure chlorine concentration.

SUMMARY OF THE INVENTION

An iodometric test device for chlorine measurement comprising a valved enclosure and incorporated therewith a starch/iodide reagent incorporated within a reduced fluid, the fluid serving to store said reagent stably, the fluid discharging said reagent in atomized form for increased sensitivity to chlorine, and the fluid shielding said reagent from interferents. Said starch/iodide reagent preferably comprises a mixture of 1-3% iodometric starch and 2-8% iodide salt in aqueous solution. The reducing fluid preferably comprises a hydrocarbon, preferably butane or isobutane, in the preferable proportion by weight of 1-4 parts hydrocarbon to 6-9 parts starch/iodide reagent. To make my invention, a valved enclosure is filled in process order with 6-8 parts starch solution, 1-4 parts hydrocarbon, then 1 part iodide solution. To use my invention for chlorine analysis, sample chlorinated water is contacted by discharged iodometric composition, whereupon said water changes color in proportion to chlorine content.

DETAILED DESCRIPTION OF THE INVENTION

In accordance with my invention, an iodometric test device, a method for making and method for using such device for chlorine measurement comprises filling a valved enclosure with a composition comprising preferably, by weight 6-9 parts aqueous starch/iodide reagent and 1-4 parts reducing fluid, such that propelled discharge of the composition into chlorinated disinfectant water produces a color proportional to chlorine content of said water. Such reagent comprises, by weight:

2-8% iodide salt, preferably potassium iodide;

1-3% starch, preferably soluble, iodometric grade;

89-97% water.

The reducing fluid comprises a high vapor pressure hydrocarbon, preferably butane or isobutane, so that the hydrocarbon serves functionally in one aspect as a reagent stabilizer against oxidants, in a second aspect as a propellant to atomize reagent discharge for greater sensitivity, and in a third aspect as a reagent entrained shield against interferents.

In accordance with my invention, a method for making a test device to measure chlorine in disinfectant water comprises filling a valved enclosure in process order with, by weight, preferably:

6-8 parts iodometric starch solution;

1-4 parts butane or isobutane;

1 part potassium iodide solution.

In accordance with my invention, a method for using the test device to measure chlorine colorimetrically in disinfectant water comprises discharge of test composition into sample water, in a preferable ratio of respectively 1:30 parts by weight, contact developing a measurable color in sample water proportional to chlorine content. The following example will clarify my invention without necessarily limiting its scope:

EXAMPLE

A 10 fluid ounce spray can is charged in order with:

(1) 0.1 ounce iodometric soluble starch in 6 ounces water;

(2) 2 ounces isobutane;

(3) 0.3 ounce potassium iodide in 1 ounce water.

To use my invention, a cupful of sample water, approximately 30 parts by weight is sprayed with 1 part reagent entrained isobutane whereupon the sample water changes color in proportion to its free chlorine content, in a range from pink at 0.4 ppm chlorine to dark blue at 2.0 ppm chlorine.

I claim:

1. A stable iodometric indicating composition in a device comprising a starch-iodide reagent incorporated within a hydrocarbon fluid, such composition comprising, by weight:

1-4 parts hydrocarbon fluid;

6-9 parts aqueous starch-iodide reagent;

such indicating composition enclosed within a valved test device, and such test device controllably discharging propelled indicating composition into contact with sample matter, thereby identifiably coloring said matter in proportion to chlorine content.

2. The stable iodometric indicating composition in accord with claim 1, wherein said hydrocarbon fluid comprises butane or isobutane.

3. The indicating composition in accord with claim 1, in which such hydrocarbon fluid is at both sufficient concentration to stabilize the starch-iodide reagent and of greater than atmospheric vapor pressure to propel hydrocarbon stabilized starch-iodide reagent into contact with sample matter.

4. The indicating composition in accord with claim 1, in which the starch iodide reagent comprises by weight:

2–8% iodide salt,;

1–3% starch,;

89–97% water.

5. The indicating composition in accord with claim 4 wherein the iodide salt is potassium iodide and the starch is soluble and iodometric grade.

6. A method for making a valved enclosure test device for measuring chlorine in disinfectant water comprising filling the valved enclosure with an iodometric indicating composition, in accord with claim 1, comprising by weight:

6–8 parts soluble, iodometric grade starch;

1–4 parts isobutane;

1 part potassium iodide solution.

7. A method for using the valved enclosure test device in accord with claim 6, in which sample water is contacted by valve controlled propelled discharge of indicating composition, in an approximate ratio of 30 parts sample water to 1 part indicating composition, such contact thereby identifiably coloring said water in proportion to chlorine content in a range from pink at 0.4 ppm to dark blue at 2 ppm.

* * * * *